US006358916B1

(12) United States Patent
Chen et al.

(10) Patent No.: US 6,358,916 B1
(45) Date of Patent: Mar. 19, 2002

(54) BIOLOGICAL ACTIVITY OF IGF-I E DOMAIN PEPTIDE

(76) Inventors: Thomas T. Chen; Maria J. M. Chen, both of 36 Hunter's Run, Storrs, CT (US) 06268; Xiuchun Tian, 131 Birch Rd., Storrs, CT (US) 06268-1505

( * ) Notice: Subject to any disclaimer, the term of this patent is extended or adjusted under 35 U.S.C. 154(b) by 0 days.

(21) Appl. No.: 09/120,818

(22) Filed: Jul. 22, 1998

(51) Int. Cl.$^7$ ............................................. A61K 38/30
(52) U.S. Cl. ............................ 514/2; 530/351; 530/399; 536/23.5
(58) Field of Search ................................ 530/351, 399; 536/23.5; 514/2

(56) References Cited

U.S. PATENT DOCUMENTS

| 5,093,317 A | 3/1992 | Lewis et al. .................. 514/12 |
| 5,476,779 A | 12/1995 | Chen et al. .............. 435/240.1 |

FOREIGN PATENT DOCUMENTS

| EP | 0 309 050 A1 | 3/1989 |
| WO | WO 89/05822 | 6/1989 |
| WO | WO 93/23067 | 11/1993 |

OTHER PUBLICATIONS

Zheng, J.L et al., "Induction of Cell Proliferation by Fibroblast and Insulin–Like Growth Factors in Pure Rat Inner Ear Epithelial Cell Cultures," *J. Neurosci.* 17(1): 216–226 (Jan. 1, 1997) (XP–002060020).

Cambrey, A.D. et al., "Insulin–like growth factor I is a major fibroblast mitogen produced by primary cultures of human airway epithelial cells," *Clincal Science* 89:611617 (1995).

Duguay, S.J. et al., "Mutational Analysis of the Insulin–like Growth Factor I Prohormone Processing Site," *J. of Biol. Chem.* 270(29):17566–17574 (1995).

Duguay, S.J. et al., "Nucleotide Sequence and Tissue Distribution of Three Insulin–Like Growth Factor I Prohormones i Salmon," *Molecular Endocrinology*, 6(8):1202–1210 (1992).

Greene, M.W. and Chen, T.T., Temporal expression pattern of insulin–like growth factor mRNA during embryonic development in a teleost, rainbow trout (*Onchorynchus mykiss*), *Mol. Marine Biol. and Biotech.* 6(2):144–151 (1997).

Hylka, V.W. and Straus, D.S., "The E–domain peptide of rat pro–insulin–like growth factor II (proIGF–II): properties of the peptide in serum and production by rat cell lines," *Biochimica et Biophysica Acta* 1051:6–13 (1990).

Siegfried, J.M. et al., "A mitogenic peptide amide encoded within the E peptide domain of the insulin–like growth IB prohormone," *Proc. Natl. Acad. Sci. USA* 89:8107–8111 (1992).

Shamblott M.J. and Chen, T.T., "Age–related and tissue–specific levels of five forms of insulin–like growth factor mRNA in a teleost," *Mol. Marine Biol. and Biotech.* 2(6):351–361 (1993).

Wallis, A.E. and Devlin, R.H., "Duplicate Insulin–Like Growth Factor–I Genes in Salmon Display Alternative Splicing Pathways," *Mol. Endocrinology* 7(3):409–422 (1993).

*Primary Examiner*—Lorraine Spector
*Assistant Examiner*—Eileen B. O'Hara
(74) *Attorney, Agent, or Firm*—Cummings & Lockwood

(57) ABSTRACT

Methods of increasing mitosis in cells; of increasing cell attachment in culture; of enhancing wound healing; and of inhibiting proliferation of malignant cells, are described, comprising administering an E domain peptide from insulin-like growth factor I (IGF-I) of a trout, or administering an E domain peptide homolog, an E domain peptide fusion protein, or a nucleic acid encoding an E domain peptide, an E domain peptide homolog or an E domain peptide fusion protein.

2 Claims, 5 Drawing Sheets

BIOLOGICAL ACTIVITY OF IGF-I E DOMAIN PEPTIDE

GOVERNMENT SUPPORT

The invention was supported, in whole or in part, by grant number 9596241 from the National Science Foundation. The U.S. Government has certain rights in the invention.

BACKGROUND OF THE INVENTION

Insulin-like growth factors (IGFs) are members of the highly diverse insulin gene family that includes insulin, IGF-I, IGF-II, relaxin, prothoraciotropic hormone (PTTH), and molluscan insulin-related peptide (Blundell, T. L. and Humbel, R. E., *Nature* 287:781–787 (1980); Ebberink, R. H. M. et al., *Biol. Bull* 177:176–182 (1989); Smit, A. B. et al., *Nature* 331:535–538 (1989)). IGFs comprise, from amino to carboxy termini, a prepeptide leader followed by a B domain, a C domain, an A domain, a D domain and a carboxy-terminal E domain. The IGFs are circulating, mitogenic peptide hormones that have an important role in stimulating growth, differentiation, metabolism and regeneration both in vitro and in vivo (Froesh, E. R., in *Insulin-like Growth Factors/Somatomediams*, de Gruyter, S. M. (ed.), New York, pp. 18–29 (1983); Lowe, M. W. Jr., in *Insulin-like Growth Factors:Molecular and Cellular Aspects*, LeRoith, D. (ed.), Boca Raton, Fla., CRC Press, pp. 49–80 (1991)). IGF-I and IGF-II are produced as prepropeptides; upon post-translation processing, the prepeptide leader sequence and the E domain peptide are cleaved from the prepropeptide to form the mature, bioactive molecule. In trout, four distinct forms of IGF-I mRNA exist (IGF Ea-1, Ea-2, Ea-3 and Ea-4), differing in the lengths of the E domain peptides (Shamblott, M. J. and Chen, T. T., *Mol. Mar. Biol. Biotechnol.* 2(6):351–361 (1993)). These four mRNA forms have different temporal expression patterns (Greene, M. W. and Chen, T. T., Mol. *Mar. Biol. Biotechnol.* 6(2):144–151 (1997)).

SUMMARY OF THE INVENTION

As described herein, the E domain peptides of rainbow trout insulin-like growth factor I (rtIGF-I) have several biological activities, including mitogenic activity, cell attachment activity, and induction of morphological changes in malignant or oncogenically-transformed cells. The present invention thus pertains to use of an E domain peptide agent, such as an E domain peptide of a trout, an E domain peptide homolog, an E domain peptide fusion protein, or a nucleic acid encoding an E domain peptide, E domain peptide homolog, or E domain peptide fusion protein. In one embodiment, the invention is drawn to methods of increasing mitosis in cells, by administering to the cells at least one E domain peptide agent, particularly Ea-2 domain peptide, Ea-3 domain peptide or Ea-4 domain peptide. In another embodiment, the invention is drawn to methods of increasing cell attachment in culture (e.g., cell culture or tissue culture), by providing to the cells an E domain peptide agent, particularly Ea-2 domain peptide and/or Ea-4 domain peptide, in the cell culture medium. The invention also provides a culture medium containing one or more E domain peptide agents (e.g., to supplement or replace fetal bovine serum). In yet another embodiment, the invention is drawn to methods of enhancing wound healing, by administering to the wound one or more E domain peptide agents. In a further embodiment, the invention is drawn to methods of inhibiting proliferation of malignant cells, either in vitro or in vivo, by administering one or more E domain peptide agents to the malignant cells.

Figure 1:
FIG. 1 is a depiction of the structure of the rainbow trout pre-pro-IGF-I polypeptide, showing the leader peptide, portion that is mature IGF-I, and the E domain peptide.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention pertains to the discovery that the E domain peptides of rainbow trout insulin-like growth factor I (rt-IGF-I) have several biological activities. The E domain peptides of rainbow trout include the Ea-1 domain peptide, RSVRAQRHTDMPRTPKEVHQKNSSRGNTGGRNYRM (SEQ ID NO:1); the Ea-2 domain peptide, RSVRAQRHT-DMPRTPKKPLSGNSHTSCKEVHQKNSS-RGNTGGRNYRM (SEQ ID NO:2); the Ea-3 domain peptide, RSVRAQRHTDMPRTPKVSTAVQSVDRG-TERRTAQHPDKTKPKKEVHQKNSSR GNTGGRNYRM (SEQ ID NO:3); and the Ea-4 domain peptide, RSVRAQRHTDMPRTPKVSTAVQNVDRG-TERRTAQHPDKTKTKKKPLSGNSHT SCKEVHQKNS-SRGNTGGRNYRM (SEQ ID NO:4). As described below, the Ea-2, Ea-3 and Ea-4 domain peptides have mitogenic activity on several types of cells, as shown by stimulation of increased incorporation of [$^3$H]-thymidine into the DNA of cells exposed to the E domain peptides, and/or by stimulation of increased total DNA content in cells exposed to the E domain peptides. In addition, the Ea-2 and Ea-4 domain peptides induce morphological change and cell attachment in cells exposed to the E domain peptides and grown in a serum-free medium. The Ea-4 domain peptide also prevented transformed cells and malignant tumor cells from forming colonies in a soft agar medium, thereby restoring the contact inhibition activity of the transformed (malignant) and tumor cells.

The invention takes advantage of these biological activities of the E domain peptides. In the methods of the invention, E domain peptides of a trout are used. As used herein, the term "E peptide" or "E domain peptide" refers to a peptide that forms an E domain of IGF-I of a trout. In a preferred embodiment, the trout is a rainbow trout, such as Onchorynchus species, and particularly *Onchorynchus mykiss*. In a particularly preferred embodiment, the E domain peptide is the Ea-1 (SEQ ID NO:1), Ea-2 (SEQ ID NO:2), Ea-3 (SEQ ID NO:3) or Ea-4 (SEQ ID NO:4) domain peptide of *Onchorynchus mykiss*. The E domain peptides can be isolated from naturally-occurring sources, chemically synthesized or recombinantly produced.

The amino acid sequence of the E domain peptide can be that of the naturally-occurring protein or can comprise alterations therein. Such alterations include conservative or non-conservative amino acid substitutions, additions and deletions of one or more amino acids; however, such alterations should preserve at least one of the biological activities of the E domain peptide as described herein, i.e., the altered or mutant E domain peptide should be an active derivative of the naturally-occurring E domain peptide. For example, the mutation(s) can preferably preserve the mitogenic activity of the native E domain peptide, or the ability of the E domain peptide to induce morphological changes or cell attachment. The presence or absence of E domain biological activity or activities can be determined by various standard functional assays such as those described below in the Examples. Moreover, amino acids which are essential for the function of the E domain peptide can be identified by methods known in the art. Particularly useful methods include identification of conserved amino acids in the family or subfamily of IGF-I proteins, site-directed mutagenesis and alanine-scanning mutagenesis (for example, Cunningham and Wells, *Science* 244:1081–1085 (1989)), crystallization and nuclear magnetic resonance. Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (*Science* 247:1306–1310(1990)).

Peptides which are at least about 70% identical, preferably at least about 80% identical, and more preferably at least about 90% identical to the trout E domain peptides described herein can also be used, provided that the peptides have at least one of the biological activities of an E domain peptide, as described herein. Such peptides are referred to herein as "E domain peptide homologs".

The E domain peptide can also be part of a fusion protein comprising the amino acid sequence of an E domain peptide or an E domain peptide homolog, fused to an additional component. Additional components, such as radioisotopes and antigenic tags, can be selected to assist in the isolation or purification of the peptide or to extend the half life of the peptide; for example, a hexahistidine tag permits ready purification by nickel chromatography. A fusion protein comprising an E domain peptide is referred to herein as an "E domain peptide fusion protein".

The trout E domain peptides, E domain peptide homologs, and E domain peptide fusion proteins described herein are referred to collectively as "E domain peptide agents." In the methods of the invention, at least one E domain peptide agent is used; more than one E domain peptide agent can also be used. If more than one E domain peptide agent is used, the agents can be different types. For example, an E domain peptide and an E domain peptide homolog can be used concurrently, as can an E domain peptide homolog and an E domain peptide fusion protein. Alternatively or in addition, if more than one E domain peptide agent is used, the agents can be of the same type. For example, two E domain peptides, such as the Ea-2 domain peptide and the Ea-4 domain peptide, can be used concurrently.

A nucleic acid encoding an E domain peptide agent can also be used in the methods of the invention. A nucleic acid encoding an E domain peptide agent can be used by itself, or can be contained in an expression vector; the term "nucleic acid encoding an E domain peptide agent" includes both the nucleic acids alone, and the nucleic acids contained in an expression vector. Many such vectors are commercially available, and other suitable vectors can be readily prepared by the skilled artisan. For example, nucleic acids encoding E domain peptides are described in Shamblott et al, *Mol. Mar. Bio. Biotech.*, 2:351–361(1993); the entire teachings of which are incorporated herein by reference. In a preferred embodiment, the nucleic acid encoding an E domain peptide agent is contained in an expression vector and is operably linked to a regulatory sequence. "Operably linked" is intended to meant that the nucleotide sequence is linked to a regulatory sequence in a manner which allows expression of the nucleic acid sequence. Regulatory sequences are art-recognized and are selected to produce a gene product or active derivative thereof. Accordingly, the term "regulatory sequence" includes promoters (e.g., a β-actin gene promoter), enhancers, and other expression control elements, such as those which are described in Goeddel, *Gene Expression Technology: Methods in Enzymology* 185, Academic Press, San Diego, Calif. (1990). For example, the native regulatory sequences or regulatory sequences native to a host cell can be employed. It should be understood that the design of the expression vector may depend on such factors as the choice of the host cell and/or the type of E domain peptide desired to be expressed. For instance, the E domain peptide agents of the present invention can be produced by ligating a nucleic acid encoding the E domain peptide agent into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2 nd Ed., ed. Sambrook et al. (Cold Spring Harbor Laboratory Press, 1989) Chapters 16 and 17). Typically, expression constructs can contain one or more selectable markers, including, but not limited to, the gene that encodes dihydrofolate reductase and the genes that confer resistance to neomycin, tetracycline, ampicillin, chloramphenicol, kanamycin and streptomycin resistance.

In one embodiment of the invention, an E domain peptide agent, or a nucleic acid encoding an E domain peptide agent, is used to increase mitosis in cells. In this embodiment, at least one E domain peptide agent (or nucleic acid encoding an E domain peptide agent) is administered to the cells. It is administered in a manner such that the E domain peptide agent comes into contact with the cells (such as by adding the E domain peptide agent to a cell culture well containing the cells of interest), or such that the nucleic acid encoding the E domain peptide agent is transfected into the cells (e.g., by electroporation, transfection using calcium chloride, rubidium chloride, calcium phosphate, or other substances; microprojectile bombardment, such as with a gene gun; or by infection where the vector is an infectious agent such as a retroviral). In a preferred embodiment, the E domain peptide agent is an E domain peptide from a trout, such as rainbow trout. In a particularly preferred embodiment, the E domain peptide agent is Ea-2 domain peptide (SEQ ID NO:2), Ea-3 domain peptide (SEQ ID NO:3) or Ea-4 domain peptide (SEQ ID NO:4). In another preferred embodiment, a nucleic acid encoding an E domain peptide agent from a trout, such as rainbow trout, is used. In a particularly preferred embodiment, the E domain peptide agent encoded by the nucleic acid is Ea-2 domain peptide (SEQ ID NO:2), Ea-3 domain peptide (SEQ ID NO:3) or Ea-4 domain peptide (SEQ ID NO:4). The E domain peptide agent, or the nucleic acid encoding the E domain peptide agent, is administered in an effective amount; that is, in an amount that is sufficient to increase mitosis. Generally, between approximately 1–200 ng/ml of E domain peptide agent is administered. In a preferred embodiment, between approximately 20–100 ng/ml of E domain peptide agent is administered; in a more preferred embodiment, approximately 40 ng/ml of E domain peptide agent is administered. An increase in mitosis can be assessed, for example, by assessing the cells for an increase in the total DNA, or for an increase in $^3$H-thymidine incorporation into DNA, as described in the Examples below.

In another embodiment of the invention, an E domain peptide agent, or a nucleic acid encoding an E domain peptide agent, is used to enhance (increase) attachment of cells in culture. In this embodiment, at least one E domain peptide agent (or nucleic acid encoding an E domain peptide agent) is administered to the cells in culture. If an E domain peptide agent is used, it is administered in a manner such that the E domain peptide agent comes into contact with the cells, such as by adding the E domain peptide agent to a cell culture well containing the cells of interest, or by including the E domain peptide agent in the cell culture medium. If a nucleic acid encoding an E domain peptide agent is used, it is administered in a manner such that the nucleic acid encoding the E domain peptide agent is transfected into the cells, such as by the methods described above. In a preferred embodiment, the E domain peptide agent is an E domain peptide from a trout, such as rainbow trout. In a particularly preferred embodiment, the E domain peptide agent is Ea-2 domain peptide (SEQ ID NO:2) or Ea-4 domain peptide (SEQ ID NO:4). In another preferred embodiment, a nucleic acid encoding an E domain peptide agent from a trout, such as rainbow trout, is used. In a particularly preferred embodiment, the E domain peptide agent is Ea-2 domain peptide (SEQ ID NO:2) or Ea-4 domain peptide (SEQ ID NO:4). The E domain peptide agent, or the nucleic acid encoding the E domain peptide agent, is administered in an effective amount; that is, in an amount that is sufficient to enhance attachment of the cells (e.g., attachment to the surface of the container in which the cells are being cultured, such as a cell culture chamber). Generally, between approximately 1–200 ng/ml of E domain peptide agent is administered. In a preferred embodiment, between approximately 20–100 ng/ml of E domain peptide agent is administered; in a more preferred embodiment, approximately 40 ng/ml of E domain peptide agent is administered. The invention also comprises a cell culture medium containing at least one E domain peptide agent.

In yet another embodiment of the invention, an E domain peptide agent, or a nucleic acid encoding an E domain peptide agent, is used to enhance (increase) wound healing. The biological properties of the E domain peptide agents (e.g., increasing mitosis and/or enhancing cell attachment) facilitate the growth of cells to fill in and repair the wound. In this embodiment, at least one E domain peptide agent (or nucleic acid encoding an E domain peptide agent) is administered to a wound. It is administered in a manner such that the E domain peptide agent comes into contact with the wound. The E domain peptide agent can be administered alone, or can be administered in a pharmaceutical composition. For instance, an E domain peptide agent can be formulated with a physiologically acceptable medium or carrier to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the E domain peptide agent in the chosen medium can be determined empirically, according to well known procedures, and will depend on the ultimate pharmaceutical formulation desired. Methods of administration include, but are not limited to, intradermal, intraocular, intramuscular, topical, intraperitoneal, subcutaneous, and intranasal. The form in which the pharmaceutical composition will be administered (e.g., solution or emulsion) will depend on the route by which it is administered. Other suitable forms of administration also include rechargeable or biodegradable devices and slow release polymeric devices. The pharmaceutical compositions can also be administered as part of a combinatorial therapy with other agents.

In a preferred embodiment, the E domain peptide agent that is used is an E domain peptide from a trout, such as rainbow trout. In a particularly preferred embodiment, the E domain peptide agent is Ea-2 domain peptide (SEQ ID NO:2) or Ea-4 domain peptide (SEQ ID NO:4). The E domain peptide agent, or the composition comprising the E domain peptide agent, is administered in an effective amount; that is, in an amount that is sufficient to enhance wound healing (stimulation of cell attachment and cell growth (cell division) to cover and fill in the wound). Generally, between approximately 1–200 ng/ml of E domain peptide agent is administered. In a preferred embodiment, between approximately 20–100 ng/ml of E domain peptide agent is administered; in a more preferred embodiment, approximately 40 ng/ml of E domain peptide agent is administered.

In yet another embodiment of the invention, an E domain peptide agent, or a nucleic acid encoding an E domain peptide agent, is used to inhibit proliferation of malignant cells, either in vitro or in vivo. Malignant cells have lost the property of contact inhibition, and grow out of control; the E domain peptide agents can reintroduce the property of contact inhibition, thereby stopping uncontrolled growth of the cells. In this embodiment, at least one E domain peptide agent (or nucleic acid encoding an E domain peptide agent) is administered to the malignant cells, in a manner such that the E domain peptide agent comes into contact with the malignant cells. For example, if the malignant cells are in culture, an E domain peptide agent can be administered by providing a culture medium comprising the E domain peptide agent. If the malignant cells are cells of a tumor in vivo, an E domain peptide agent is administered, for example, by injection into the tumor or other appropriate means. A nucleic acid encoding an E domain peptide agent can be administered to malignant cells in culture by transfecting the malignant cells, as described above; a nucleic acid encoding an E domain peptide agent can be administered to cells of a tumor in vivo by a similar appropriate means.

For inhibition of proliferation of malignant cells in a tumor, the E domain peptide agent or nucleic acid encoding an E domain peptide agent can be administered alone, or can be administered in a pharmaceutical composition as described above. In a preferred embodiment, the E domain peptide agent that is used is an E domain peptide from a trout, such as rainbow trout. In a particularly preferred embodiment, the E domain peptide agent is Ea-2 domain peptide (SEQ ID NO:2) or Ea-4 domain peptide (SEQ ID NO:4). In another preferred embodiment, a nucleic acid encoding an E domain peptide agent from a trout, such as rainbow trout, is used. In a particularly preferred embodiment, the E domain peptide agent encoded by the nucleic acid is Ea-2 domain peptide (SEQ ID NO:2) or Ea-4 domain peptide (SEQ ID NO:4) The E domain peptide agent, or the composition comprising the E domain peptide agent, is administered in an effective amount; that is, in an amount that is sufficient to inhibit proliferation of the malignant cells. Inhibition of proliferation is indicated, for example, by the return of contact inhibition of the malignant cells, as described in the Examples below. For example, if at least about 70%, more preferably at least about 80%, and even more preferably at least about 90% of the cells regain contact inhibition, then inhibition of proliferation has occurred. A slowing or cessation of growth of malignant cells, or of a tumor, is also indicative of inhibition of proliferation. Generally, between approximately 1–200 ng/ml of E domain peptide agent is administered. In a preferred embodiment, between approximately 20–100 ng/ml of E domain peptide agent is administered; in a more preferred embodiment, approximately 40 ng/ml of E domain peptide agent is administered.

The following Examples are offered for the purpose of illustrating the present invention and are not to be construed to limit the scope of this invention. The teachings of all references cited herein are hereby incorporated herein by reference.

EXAMPLES

Example 1

Preparation of Recombinant Rainbow Trout IGF-I E Domain Peptides

There are four different species of IGF-I mRNA in rainbow trout (*Oncorhynchus mykiss*) (Shamblott, M. J. and T. T. Chen, *Mol. Mar. Biol. Biotechnol.* 2(6):351–361 (1993), the entire teachings of which are incorporated herein by reference). These four different species of niRNA encode four pre-pro-IFG-I polypeptides with differences residing in the E domain region (FIG. 1). The four different E domain peptides are: the Ea-1 peptide, RSVRAQRHTDMPRTP-KEVHQKNSSRGNTGGRNYRM (SEQ ID NO:1); the Ea-2 peptide, RSVRAQRHTDMPRTPKKPLSGNSH-TSCKEVHQKNSSRGNTGGRNYRM (SEQ ID NO:2); the Ea-3 peptide, RSVRAQRHTDMPRTPKVSTAVQSVDRG-TERRTAQHPDKTKPKKEVHQKNSSR GNTGGRNYRM (SEQ ID NO:3); and the Ea-4 peptide, RSVRAQRHTDM-PRTPKVSTAVQNVDRGTERRTAQHPDKT-KTKKKPLSGNSHT SCKEVHQKNSSRGNTGGRNYRM (SEQ ID NO:4).

To investigate the biological activities of the E domain polypeptides, recombinant IGF-I E domain polypeptides were prepared by expressing the E domain cDNA in a pET15b vector (Novagen, Madison, Wis.) in *E. coli* cells. The pET15 b vector was used because it adds six histidine residues at the N-terminus of a protein expressed by the pET15b vector; these histidine residues facilitate purification of expressed proteins by metal affinity chromatography on a nickel column. To express the E domain cDNA in the pET15b vector, vectors containing cDNA for each of the four E domain polypeptides were prepared. Since the N- and C-termini of each of the E domains share identical amino acid sequences, a set of oligonucleotide primers (5'-CTACTACATATGCGCTCAGTGCGCGCA-3' (SEQ ID NO:5), and 5'-CTCCCCGATATCCTACATTCGGT AGTTTCT-3' (SEQ ID NO:6)) specific for the N- and C-termini, and containing sequences for restriction enzyme recognition sites for Nde I and Bam H1, were used in the polymerase chain reaction (PCR) to amplify the IGF-I E domain cDNAs from the four fall-length IGF-I cDNA subformis. The resulting cDNAs were clones into a PBS SKII plasmid (Stratagene, Calif.), recombinant clones were selected and verified by nucleotide sequence determination. The E domain cDNA inserts were released from each clone by digestion with restriction enzymes Nde I and Bam HI, and the resulting DNA inserts were then cloned into the multiple cloning site of the pET15b vector that is downstream of the his tac sequence. *E. coli* (strain BL21, Novagen, Inc., Madison, Wis.) were transformed with the vectors, grown in nutrient broth (Gibco) to an $OD_{600}$ of 0.6 to 1.0, and induced by isopropylthiogalactoside (IPTG) at 0.1 mM (final concentration) for 2 hours at 37° C. The cells were then harvested, resuspended in binding buffer (5 mM imidazole, 0.5 M NaCl, 20 mM Tris-HCl, pH 7.9, chemicals from Sigma, St. Louis, Mo.) and sonicated at 40 watts for 40 seconds. Cell debris was removed by centrifuging the mixture at 39×g for 20 minutes.

To separate the E domain polypeptides from bacterial proteins, a protocol of histidine-binding column separation (Novagen) was followed. Briefly, the supernatant was applied to a His-bind column precharged with 50 mM $NiSO_4$. Ni++ in the column selectively binds to the peptides containing the series of histidine residues. The column was then washed with 10 bed volumes of the binding buffer (5 mM imidazole, 0.5 M NaCl, 20 mM Tris-HCl, pH 7.9) and 6 bed volumes of a washing buffer (60 mM imidazole, 0.5 M NaCl, 20 mM Tris-HCl, pH 7.9). The imidazole molecule resembles the molecular structure of histidine, and replaces weakly bound histidine-containing polypeptides on the column. The E-domain polypeptides are then eluted from the column with Tris-HCl buffer containing 1.0 M imidazole (1 M imidazole, 0.5 M NaCl, 20 mM Tris-HCl, pH 7.9). Imidazole in the eluant was removed by dialyzing the eluant in a phosphate buffer (0.1 M, pH 7.5).

The identities of the recombinant clones were verified by nucleotide sequence determination. The addition of the 6-histidine tag at the N-terminus of the E domain peptides resulted in an addition of 21 amino acid residues at the N-terminus of each expressed peptide, thus giving rise to 68, 83 and 95 amino acid residues for Ea-2, Ea-3, and Ea-4. The likely reason that the Ea-1 peptide was not isolated, is that it is degraded in the *E. coli* cells due to its short length.

Example 2

Assessment of Mitogenic Activity of E domain Polypeptides

Two different methods were used to determine the mitogenic activity of E-domain polypeptides: (1) stimulation of an increase in total DNA content and (2) stimulation of incorporation of [$^3$H]-thymidine into DNA.

Stimulation of an Increase in Total DNA Content in NIH3T3 Cells

Approximately $1 \times 10^4$ NIH3T3 cells (ATCC deposit number CCL163) were plated in each well of a 96-well tissue culture chamber in F12/DME medium (GibcoBRL) supplemented with 5 µg/ml fibronectin, 1 µM dexamethosone, 5 ng/ml bFGF, 10 mg/ml transferrin and 100 µg/ml BSA.

Figure 2:
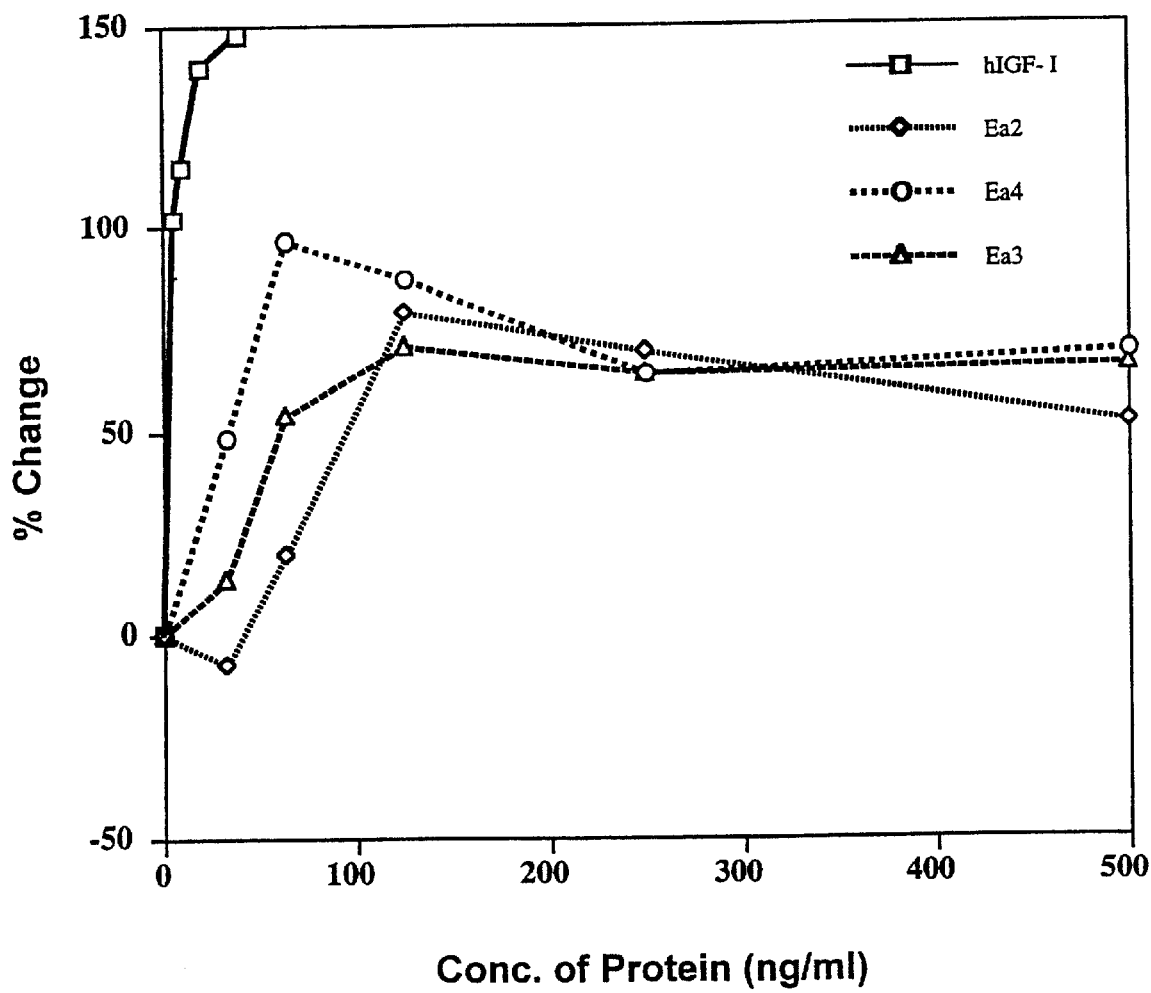
FIG. 2 is a graphic representation of the mitogenic effect of rainbow trout IGF-I E domain peptides on NIH3T3 cells. Squares, recombinant human IGF-I (hIGF-I); diamonds, Ea-2 domain peptide; triangles, Ea-3 domain peptide; and circles, Ea-4 domain peptide.

Immediately after plating, various concentrations of E-domain polypeptides (0, 15.6, 31.25, 62.4, 125, 250, 500 and 1000 ng/ml) were added to the culture wells. The cells were then incubated at 37° C. for 72 hours in an incubator equilibrated with 5%] $CO_2$. Various concentrations (0.1 ng–20 ng/ml) of recombinant human IGF (hIGF) (Sigma, St. Louis, Mo.) were used as positive controls, and bacterial extracts without E-domain polypeptides were used as negative controls. Each concentration of the E-domain polypeptide was tested in 6 duplicate wells, and the experiments were repeated at least four times. At the end of incubation, cells from each well were harvested and dissolved in 0.1SDS solution, and the total DNA was stained with Hoiest stain (H33258, Sigma, St. Louis, Mo.) for quantitative measurement in a multi-well plate reader (CytoFluor II; Farmingham, Mass.) with a 360 nm excitation wave length and a 460 nm emission wavelength. Known amounts of salmon sperm DNA were used to construct standard curves. Mitogenic effect of E-domain polypeptides was expressed in terms of percent change in fluorescence units, calculated as follows:

% change=[(FuS−FuC)/FuC]×100% where FuS=Fluorescence reading of E-domain peptide-treated samples, and FuC=Fluorescence reading of negative control samples. Results, shown in FIG. 2, indicated that Ea-2, Ea-3 and Ea-4 all possess high mitogenic activity. Squares, hIGF-I; diamonds, Ea-2; triangles, Ea-3; and circles, Ea-4.

Stimulation of Incorporation of [$^3$H]-thymidine into DNA in NIH3T3 Cells

Medium conditions for this assay were identical to those described above in relation to stimulation of an increase in total DNA content. Eighteen hours prior to harvesting, cells were pulse-labeled with 0.5 $\mu$Ci/well of [methyl-3H]-thymidine (Amersham Laboratories, Arlington Heights, Ill.). Cells were harvested, lysed in water, and the radiolabeled DNA was collected on glass fiber filters using a cell harvester (Initech Biosystems International Inc., Lansing, Mich.). The radioactivity was determined with a scintillation counter. The mitogenic activity of the Ea-4 domain polypeptide was calculated as follows:

% change=[(CPM of E-domain polypeptide-treated cells−CPM of negative control)/CPM of negative control]×100%.

These results also indicated that Ea-4 polypeptide possessed high mitogenic activity.

Mitogenic Activity of Ea-4 Polypeptide in 293GP, MCF-7 and CMEC Cells

Experiments were conducted with a transformed human cell line (293GP, Dr. Jean C. Burns, UCSD), a human mammary gland tumor cell line (MCF-7, ATCC deposit number HTB22), and a primary goat mammary gland cell line (CMEC, From Dr. Tom Young and Alex Pantschenko, Pathobiology Department of University of Connecticut), to examine stimulation of total DNA content increase. The experiments were performed as described above for NIH3T3 cells. The mitogenic effect of Ea-4 polypeptide on 293GP, MCF-7 and CMEC cells was expressed as a percent of maximum response, calculated as follows:

% maximum response=[(FuS=FuC)/(FuM−FuC)]×100% where FuS=Fluorescence reading of Ea-4 polypeptide-treated samples; FuC=Fluorescence reading of negative control samples; and FuM=Fluorescence reading of cells cultured in 5% bovine fetal serum. Bovine fetal serum samples were used as a positive control for the maximum response.

Figure 3:
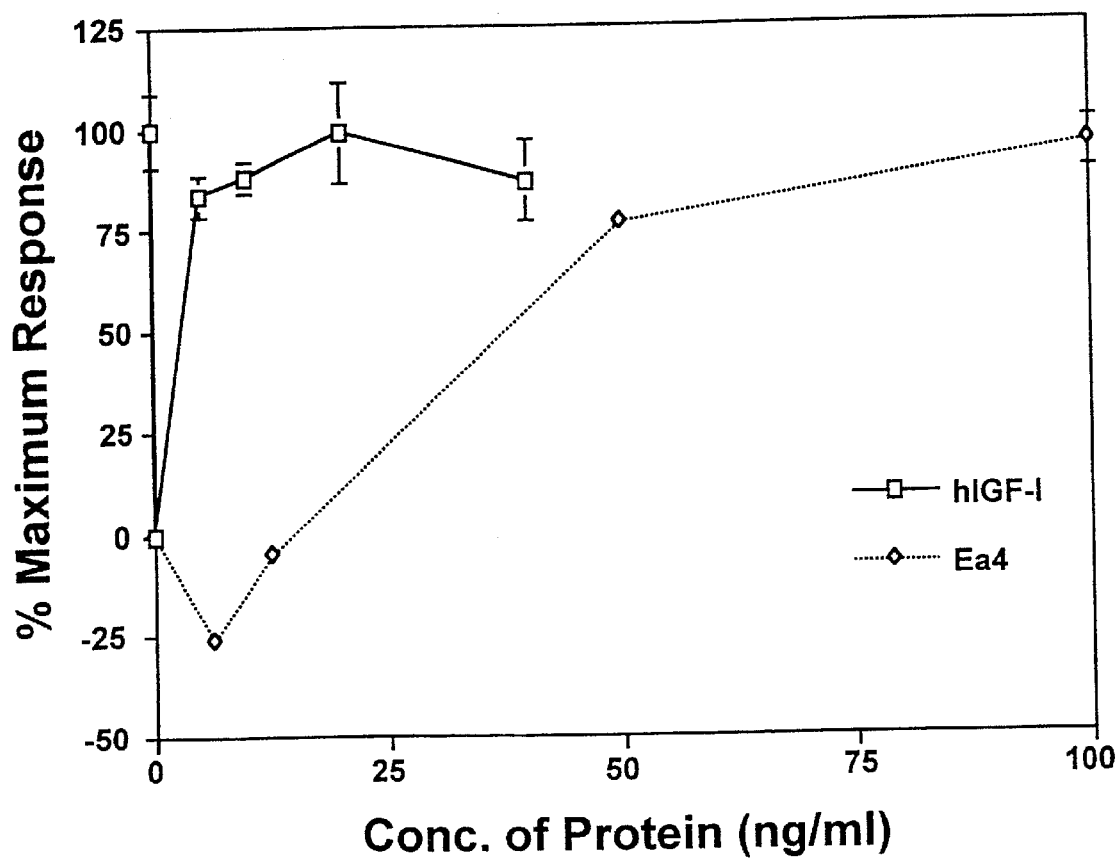
FIG. 3 is a graphic representation of the mitogenic effect of human IGF-I (hIGF-1) and rainbow trout IGF-I Ea-4 domain peptide on 293GP cells. Squares, hIGF-I; diamonds, Ea-4 domain peptide.
Figure 4:
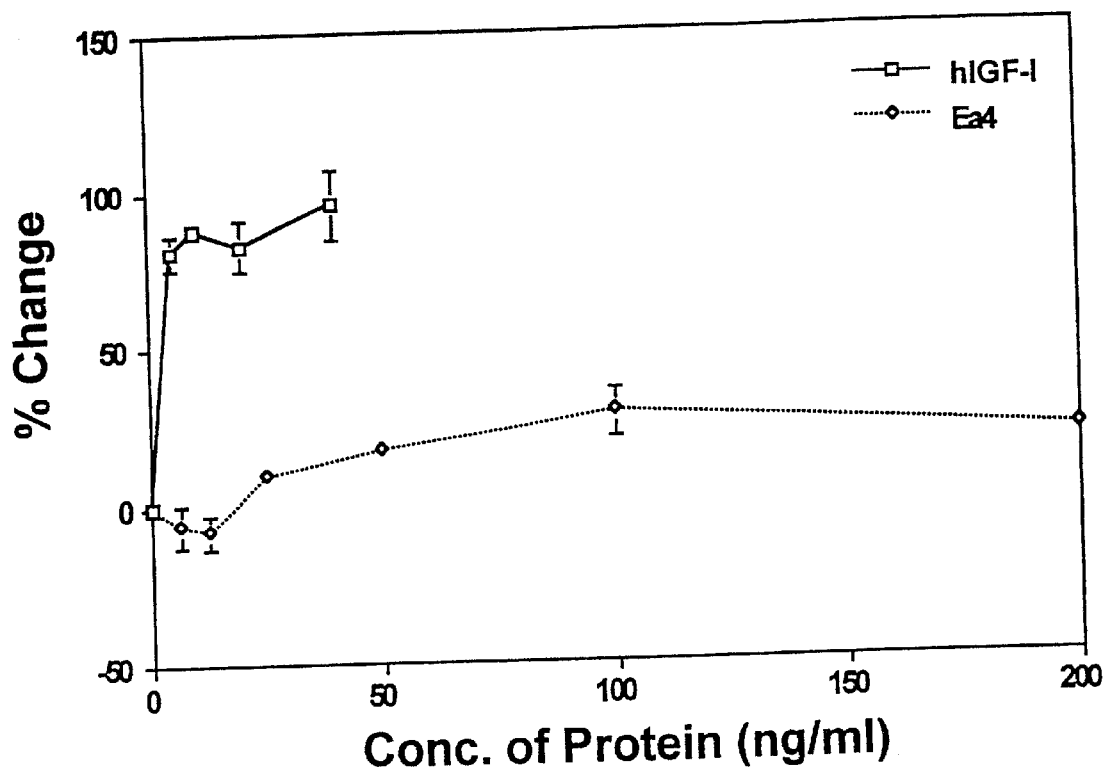
FIG. 4 is a graphic representation of the mitogenic effect of human IGF-I (hIGF-I) and rainbow trout IGF-I Ea-4 domain peptide on MCF-7 cells. Squares, hIGF-I; diamonds, Ea-4 domain peptide.
Figure 5:
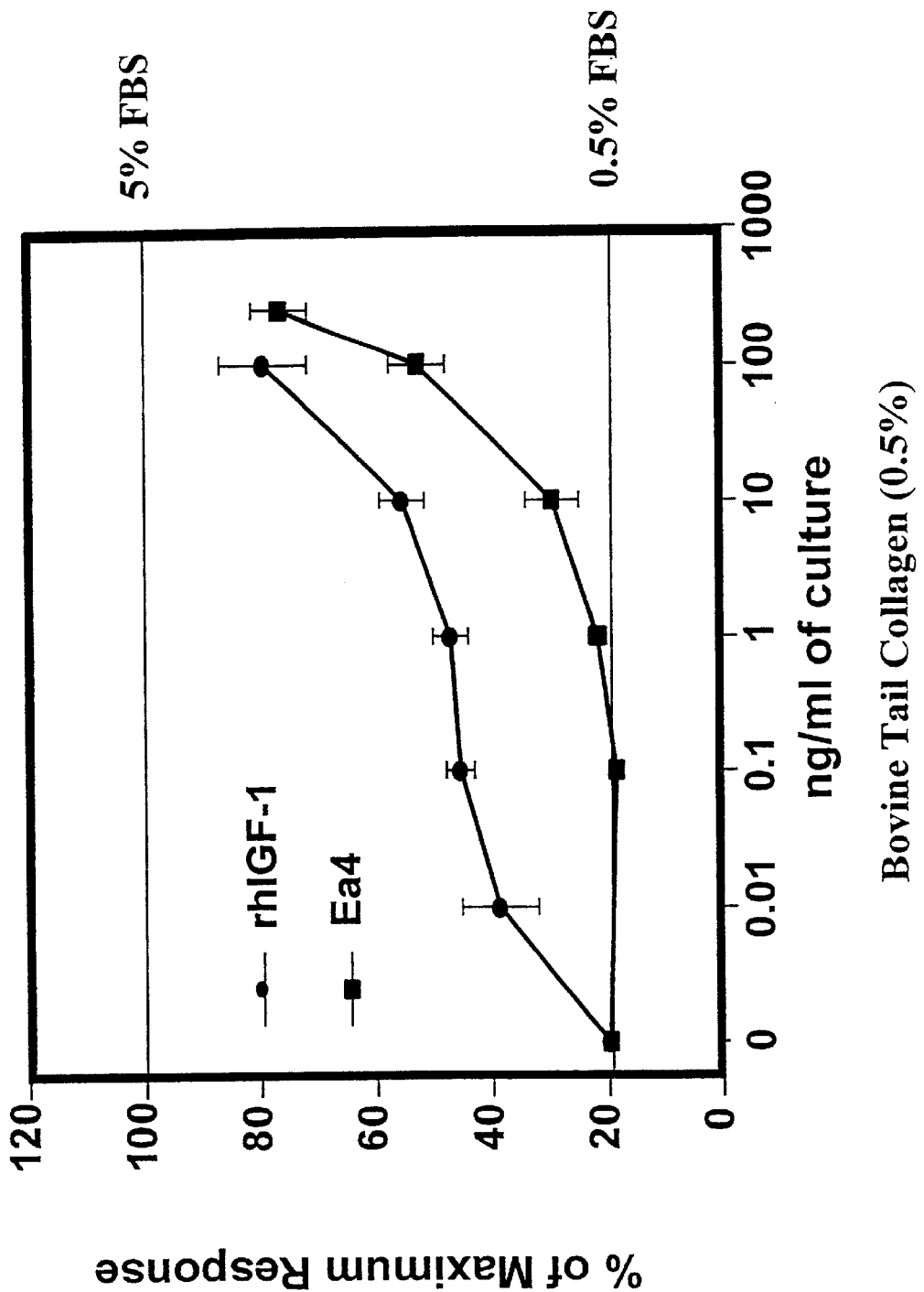
FIG. 5 is a graphic representation of the mitogenic effect of human IGF-I (hIGF-I) and rainbow trout IGF-I Ea-4 domain peptide on caprine mammary gland epithelial cell (CMEC) culture containing 0.5% bovine tail collagen. Squares, hIGF-I; diamonds, Ea-4 domain peptide.

Results, shown in FIG. 3 (293GP cells), FIG. 4 (MCF-7 cells), and FIG. 5 (CMEC cells), demonstrated that Ea-4 polypeptide possessed high mitogenic activity in these additional cell lines.

Example 3

Induction of Morphological Change and Cell Attachment Activity

Induction of morphological change and cell attachment activity by the Ea-4 polypeptide was assessed in 293GP, MCF-7 and CMEC cells. Cells were cultured in 6-well tissue culture chambers (Corning) with or without acid-washed cover slips under the same medium conditions as described in the mitogenic assays above (F12/DME medium (GibcoBRL) supplemented with 5 $\mu$/ml fibronectin, 1 $\mu$M dexamethosone, 5 ng/ml bFGF, 10 mg/ml transferrin and 100 $\mu$g/ml BSA). The optimal dose of Ea-4 polypeptide was determined by testing various doses of the Ea-4 polypeptide on the induction of the morphological changes and selecting the dose that resulted in maximum changes. Various doses of a-aminitin or cyclohexamide (0.1, 1.0, 10.0 and 100 $\mu$g/ml) were added to the culture media, and the effect of these compounds on the inhibition of induction of morphological changes was scored 24 hours after the addition of the inhibitors. Cell cultures without inhibitors were used as positive controls of the effects of Ea-4 polypeptide on induction of morphological changes. Incubation of 293GP, MCG-7 or CMEC in a serum-free medium containing the optimal dose of Ea-4 polypeptide (40 ng/ml) resulted in extension and attachment of cells to the culture chambers (data not shown). For time course studies, cells were observed under an Olympus research microscope with either the regular phase contrast objectives or differential interference phase contrast objectives, The time course study on attachment of 293GP cells exposed to 50 ng/ml Ea-4 polypeptide showed that attachment was initiated one hour after the addition of the Ea-4 polypeptide, and that fall morphological change and cell attachment were achieved 10 hours after the addition of the Ea-4 polypeptide. Even in the presence of fetal bovine serum, Ea-4 is still effective in inducing attachment in 293GP cells. However, Ea-4 induced cell attachment is inhibited by treatment with $\alpha$-aminitin or cycloheximide, suggesting that the activities of morphological change and cell attachment require expression of new genes (data not shown).

Ea-2 and Ea-3 polypeptides were also tested for induction of morphological change and cell attachment, as described above for Ea-4 polypeptide. Results showed that while Ea-2 polypeptide induces morphological changes in NIH3T3 cells, 293 GP cells, MCF-7 cells, CMEC cells, and HT cells (Dr. Larry Hightower, University of Connecticut), the Ea-3 polypeptide failed to induce any morphological changes in any of these cell lines.

Example 4

Assay for Colony Formation

Colony formation assays were conducted to determine whether 293GP and MCF-7 cells could still form colonies in soft agar containing Ea-4 polypeptide. The assays were conducted in 6-well tissue culture chambers (Corning). The basal layer medium was made of F12/DME medium (GibcoBRL) containing 0.5% bacto-agar (GibcoBRL). Test cells (2×10⁴ cells) were mixed in F12/DME medium containing 0.4% bacto-agar, supplement (5 µg/ml fibronectin, 1 µM dexamethosone, 5 ng/ml bFGF, 10 mg/ml transferrin and 100 µ/ml BSA), and Ea-4 polypeptide (40 ng/ml or 80 ng/ml), and were laid over the basal layer. Each plate was further over-laid with 1 ml of F12/DME liquid medium supplemented with 40 ng/ml Ea-4 polypeptide. The cultures were incubated at 37° C. in an incubator equilibrated with 5% $CO_2$. The liquid medium layer was replaced with fresh medium containing Ea-4 polypeptide once every 48-hour interval. The cultures were observed periodically under an inverted microscope equipped with a CDC camera. Cell mass that contained 50 cells or more was scored as a colony. Results (data not shown) indicated that Ea-4 polypeptide prevented 293GP and MCF-7 cells from forming colonies in a medium containing soft agar. This observation suggests that Ea-4 polypeptide is able to restore the "lost" contact inhibition activity of 293GP and MCF-7 cells.

The same colony formation assay was also performed, using Ea-2 polypeptide instead of Ea-4 polypeptide. Results (data not shown) indicated that Ea-2 polypeptide, like Ea-4 polypeptide, prevented 293GP and MCF-7 cells from forming colonies in a medium containing soft agar. This observation suggests that Ea-2 polypeptide is also able to restore the "lost" contact inhibition activity of 293GP and MCF-7 cells.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of increasing mitosis in cells, said method comprising administering to the cells an effective amount of at least one E:domain peptide of a rainbow trout insulin-like growth factor-I selected from the group comprising: Ea-2 domain peptide (SEQ ID NO:2) Ea-3 domain peptide (SEQ ID NO:3) and Ea-4 domain peptide (SEQ ID NO:4).

2. A method of enhancing attachment of cells in culture to a surface of a cell culture container, said method comprising providing to the cells in culture an effective amount of at least one E-domain peptide of a rainbow trout insulin-like growth factor-I selected from the group comprising: Ea-2 domain peptide (SEQ ID NO:2) and Ea-4 domain peptide (SEQ ID NO:4).

* * * * *

SEQUENCE LISTING

```
<160> NUMBER OF SEQ ID NOS: 6

<210> SEQ ID NO 1
<211> LENGTH: 35
<212> TYPE: PRT
<213> ORGANISM: Oncorhynchus mykiss

<400> SEQUENCE: 1

Arg Ser Val Arg Ala Gln Arg His Thr Asp Met Pro Arg Thr Pro Lys
1               5                   10                  15

Glu Val His Gln Lys Asn Ser Ser Arg Gly Asn Thr Gly Gly Arg Asn
            20                  25                  30

Tyr Arg Met
        35

<210> SEQ ID NO 2
<211> LENGTH: 47
<212> TYPE: PRT
<213> ORGANISM: Oncorhynchus mykiss

<400> SEQUENCE: 2

Arg Ser Val Arg Ala Gln Arg His Thr Asp Met Pro Arg Thr Pro Lys
1               5                   10                  15

Lys Pro Leu Ser Gly Asn Ser His Thr Ser Cys Lys Glu Val His Gln
            20                  25                  30

Lys Asn Ser Ser Arg Gly Asn Thr Gly Gly Arg Asn Tyr Arg Met
        35                  40                  45

<210> SEQ ID NO 3
<211> LENGTH: 62
<212> TYPE: PRT
<213> ORGANISM: Oncorhynchus mykiss

<400> SEQUENCE: 3

Arg Ser Val Arg Ala Gln Arg His Thr Asp Met Pro Arg Thr Pro Lys
1               5                   10                  15

Val Ser Thr Ala Val Gln Ser Val Asp Arg Gly Thr Glu Arg Arg Thr
            20                  25                  30

Ala Gln His Pro Asp Lys Thr Lys Pro Lys Lys Glu Val His Gln Lys
        35                  40                  45

Asn Ser Ser Arg Gly Asn Thr Gly Gly Arg Asn Tyr Arg Met
    50                  55                  60
```

<210> SEQ ID NO 4
<211> LENGTH: 74
<212> TYPE: PRT
<213> ORGANISM: Oncorhynchus mykiss

<400> SEQUENCE: 4

Arg Ser Val Arg Ala Gln Arg His Thr Asp Met Pro Arg Thr Pro Lys
 1               5                  10                  15

Val Ser Thr Ala Val Gln Asn Val Asp Arg Gly Thr Glu Arg Arg Thr
            20                  25                  30

Ala Gln His Pro Asp Lys Thr Lys Thr Lys Lys Pro Leu Ser Gly
        35                  40                  45

Asn Ser His Thr Ser Cys Lys Glu Val His Gln Lys Asn Ser Ser Arg
    50                  55                  60

Gly Asn Thr Gly Gly Arg Asn Tyr Arg Met
65                  70

<210> SEQ ID NO 5
<211> LENGTH: 27
<212> TYPE: DNA
<213> ORGANISM: Artificial Sequence
<220> FEATURE:
<223> OTHER INFORMATION: derived from Oncorhynchus mykiss

<400> SEQUENCE: 5
ctactacata tgcgctcagt gcgcgca                                      27

<210> SEQ ID NO 6
<211> LENGTH: 30
<212> TYPE: DNA
<213> ORGANISM: Artificial Sequence
<220> FEATURE:
<223> OTHER INFORMATION: Derived from Oncorhynchus mykiss

<400> SEQUENCE: 6
ctccccgata tcctacattc ggtagtttct                                   30